United States Patent
Takasugi

(10) Patent No.: US 11,662,401 B2
(45) Date of Patent: May 30, 2023

(54) MAGNETIC SENSOR, MAGNETIC DETECTION DEVICE AND MAGNETIC DETECTION SYSTEM

(71) Applicant: TDK Corporation, Tokyo (JP)

(72) Inventor: Keisuke Takasugi, Tokyo (JP)

(73) Assignee: TDK Corporation, Tokyo (JP)

( * ) Notice: Subject to any disclaimer, the term of this patent is extended or adjusted under 35 U.S.C. 154(b) by 0 days.

(21) Appl. No.: 17/156,741

(22) Filed: Jan. 25, 2021

(65) Prior Publication Data
US 2021/0231754 A1     Jul. 29, 2021

(30) Foreign Application Priority Data

Jan. 29, 2020 (JP) .............................. JP2020-012560

(51) Int. Cl.
    *G01R 33/09*      (2006.01)
    *G01N 33/543*      (2006.01)
    *G01R 33/12*      (2006.01)

(52) U.S. Cl.
CPC ..... *G01R 33/091* (2013.01); *G01N 33/54326* (2013.01); *G01R 33/1269* (2013.01)

(58) Field of Classification Search
CPC .. G01R 33/091; G01R 33/1269; G01R 33/09; G01N 33/54326; G01N 33/5434
USPC .................................................... 324/207.21
See application file for complete search history.

(56) References Cited

U.S. PATENT DOCUMENTS

| | | | |
|---|---|---|---|
| 6,184,680 B1 * | 2/2001 | Shinoura ................ | G01D 5/142 324/252 |
| 7,377,333 B1 * | 5/2008 | Sugiura ............... | E21B 17/1014 175/45 |
| 8,274,766 B2 * | 9/2012 | Fukuzawa .......... | H01F 10/3222 360/324.11 |
| 9,964,601 B2 * | 5/2018 | Shikama ............ | G01R 33/0011 |

(Continued)

FOREIGN PATENT DOCUMENTS

| | | |
|---|---|---|
| JP | 5161459 B2 | 6/2007 |
| JP | 2014-508941 A | 4/2014 |

(Continued)

OTHER PUBLICATIONS

English machine translation of Japanese Office Action dated Apr. 26, 2022 in corresponding Japanese Patent application No. 2020-012560.

*Primary Examiner* — Christopher P McAndrew
(74) *Attorney, Agent, or Firm* — Posz Law Group, PLC

(57) ABSTRACT

A magnetic sensor includes a substrate having a first surface and a second surface, which is opposite the first surface, and a detection unit provided on the first surface. The detection unit includes a magnetoresistive effect element, the resistance value of which changes in accordance with an input magnetic field, provided on the first surface, and a protective layer that covers at least the magnetoresistive effect element. The magnetoresistive effect element is configured in a linear shape extending in a first direction on the first surface. The detection unit has a first width, which is a length in a second direction, orthogonal to the first direction, and a second length, which is greater than the first width. The first width is the length of the detection unit on the first surface, and the second width is the length of the top surface of the detection unit.

13 Claims, 11 Drawing Sheets

(56) References Cited

U.S. PATENT DOCUMENTS

| | | | |
|---|---|---|---|
| 2002/0003685 A1* | 1/2002 | Takahashi | G11B 5/3909 360/327.3 |
| 2002/0014408 A1 | 2/2002 | Schroeder | |
| 2002/0160548 A1* | 10/2002 | Fukunaka | G01R 33/09 438/51 |
| 2005/0087000 A1* | 4/2005 | Coehoorn | B82Y 25/00 73/53.01 |
| 2006/0132983 A1* | 6/2006 | Osugi | G01R 33/09 |
| 2006/0202291 A1* | 9/2006 | Kolb | H01L 23/5226 257/E27.005 |
| 2007/0264422 A1* | 11/2007 | Zimmer | G11C 11/14 427/127 |
| 2009/0104707 A1* | 4/2009 | Wang | G01N 33/54326 436/151 |
| 2009/0152657 A1* | 6/2009 | Suh | G01R 33/1269 257/E29.323 |
| 2013/0113468 A1* | 5/2013 | Gao | G01D 5/145 73/152.28 |
| 2014/0154454 A1* | 6/2014 | Ueki | C09K 3/1009 977/773 |
| 2016/0084077 A1* | 3/2016 | Lehr | E21B 21/103 367/83 |
| 2017/0356968 A1* | 12/2017 | Schaller | G01R 33/07 |
| 2018/0006214 A1* | 1/2018 | Nakamura | H01L 43/08 |
| 2018/0299407 A1 | 10/2018 | Haratani et al. | |
| 2019/0154676 A1 | 5/2019 | Yuga et al. | |
| 2019/0242957 A1* | 8/2019 | Furuichi | H01F 10/3286 |
| 2020/0190970 A1* | 6/2020 | Alvarez | E21B 47/10 |

FOREIGN PATENT DOCUMENTS

| | | |
|---|---|---|
| JP | 6101215 B2 | 4/2014 |
| JP | 6043395 B2 | 9/2015 |
| WO | 2005/047864 A2 | 5/2005 |
| WO | 2009/086320 A1 | 7/2009 |
| WO | 2012/122536 A2 | 9/2012 |
| WO | 2017/029943 A1 | 2/2017 |
| WO | 2017/082227 A1 | 5/2017 |

* cited by examiner

MAGNETIC SENSOR, MAGNETIC DETECTION DEVICE AND MAGNETIC DETECTION SYSTEM

CROSS REFERENCE TO RELATED APPLICATION

This application is based on and claims priority to Japanese Patent Application No. 2020-012560 filed on Jan. 29, 2020, the disclosure of which is incorporated herein by reference.

BACKGROUND

The present invention relates to a magnetic sensor, a magnetic detection device and a magnetic detection system.

As a quantitative immunoassay, radio immunoassay (RIA; immunoradiometric assay (IRMA)) is known. In this method, it is possible to label competitive antigens or antibodies and quantitatively measure antigens from measurement results of specific radioactivity, through radionuclides. Immunoassaying is a method of labeling target objects such as antigens or the like and accomplishing indirect measurement. This method is highly sensitive and thus makes significant contributions in clinical diagnoses but has the drawback that it is necessary to ensure radionuclide safety and thus designated facilities and devices are necessary. Hence, as a method that is easier to use, a method using a biosensor that uses magnetic beads or the like as indicators has been proposed (see Patent Literature 1~4).

A conventional biosensor is provided with a substrate, a magnetoresistive effect element such as a GMR element or the like provided on the substrate, and a protective film that covers the magnetoresistive effect element. When a magnetic field is applied after magnetic beads having an affinity for biomolecules in samples are captured on a protective layer via the biomolecules, a stray magnetic field is generated from the magnetic beads. The resistance value of the magnetoresistive effect element changes due to this stray magnetic field being input into the magnetoresistive effect element, and it is possible to indirectly detect the biomolecules based on this resistance value change.

PATENT LITERATURE

PATENT LITERATURE 1 Japanese patent 5161459
PATENT LITERATURE 2 Japanese patent 6043395
PATENT LITERATURE 3 Japanese patent 6101215
PATENT LITERATURE 4 International release 2017/82227 pamphlet When the above-described biosensor is used in detecting biomolecules in a sample, the biomolecules are captured on the surface of the protective layer when a sample including the biomolecules that are the detection target is caused to contact the biosensor. Furthermore, after magnetic beads and the biomolecules captured on the surface of the protective layer are caused to bond, excess biomolecules not captured in the protective layer and magnetic beads are selectively removed by a gradient magnetic field or washing or the like, and the resistance value change of the magnetoresistive effect element is measured.

However, in a conventional biosensor, a portion of the biomolecules captured in the protective layer and the magnetic beads are removed through applying of a gradient magnetic field or washing or the like. Through this, there are cases in which the resistance value of the magnetoresistive effect element has difficulty making sufficient change to detect the biomolecules, creating the problem that variations arise in detection results. In particular, in cases in which a sample having a low biomolecule concentration is used and this biomolecule is to be detected, the problem arises that variations in the detection results become large.

In consideration of the foregoing, it is an object of the present invention to provide a magnetic sensor having a magnetoresistive effect element capable of detecting with high accuracy substances that are the detection target using magnetic beads, a magnetic detection device, and a magnetic detection system.

SUMMARY

To resolve the above-described problem, the present invention provides a magnetic sensor used in detecting detection target substances in a sample, the magnetic sensor including a substrate having a first surface and a second surface, which is opposite the first surface, and a detection unit provided on the first surface of the substrate. The detection unit includes a magnetoresistive effect element, the resistance value of which changes in accordance with an input magnetic field, provided on the first surface of the substrate, and a protective layer that covers at least the magnetoresistive effect element. The magnetoresistive effect element is configured in a linear shape extending in a first direction on the first surface of the substrate. The detection unit has a first width and a second width, which are lengths in a second direction, orthogonal to the first direction. The first width is the length of the detection unit on the first surface of the substrate. The second width is a length of the top surface of the detection unit positioned above the first surface along a third direction orthogonal to the first surface of the substrate; and the second width is greater than the first width.

In the above-described magnetic sensor, when viewing a cross-section along the second direction, the protective layer includes a first protective layer, which is positioned on the top surface of the magnetoresistive effect element, and a second protective layer, which is positioned along the side surface of the magnetoresistive effect element, and the thickness of the second protective layer on the top surface side of the magnetoresistive effect element can be greater than the thickness of the second protective layer on the first surface of the substrate.

In the above-described magnetic sensor, the ratio of the thickness of the second protective layer on the top surface side of the magnetoresistive effect element to the thickness of the second protective layer on the first surface of the substrate can be 1:0.05~1:0.95, and the ratio of the thickness of the first protective layer to the thickness of the second protective layer on the top surface side of the magnetoresistive effect element can be 1:0.05~1:1.

In the above-described magnetic sensor, the angle of the side surface of the magnetoresistive effect element with respect to the first surface of the substrate can be 90~135°, the protective layer may be a layered structure having a plurality of layers, the magnetoresistive effect element may be a GMR element, and the detection target substance may be a biomolecule.

The present invention provides a magnetic detection device including the above-described magnetic sensor and a support unit that supports the magnetic sensor. In the above-described magnetic detection device, a probe capable of bonding specifically with the detection target substance may be present on the surface of the protective layer.

The present invention provides a magnetic detection system including the above-described magnetic detection device, a magnetic field generation unit and a holding unit capable of holding the sample. The magnetic detection device is provided such that the magnetic sensor can contact the sample held in the holding unit, and the magnetic field generation unit is provided such that a magnetic field is applied on the magnetic sensor in contact with the sample held in the holding unit. In the above-described magnetic sensor, the ratio of the thickness of the second protective layer on the top surface side of the magnetoresistive effect element to the thickness of the second protective layer on the first surface of the substrate can be 1:0.05~1:0.95, and the ratio of the thickness of the first protective layer to the thickness of the second protective layer on the top surface side of the magnetoresistive effect element can be 1:0.05~1:1.

With the present invention, it is possible to provide a magnetic sensor having a magnetoresistive effect element capable of detecting with high accuracy substances that are the detection target using magnetic beads, and a magnetic detection device and a magnetic detection system.

DETAILED DESCRIPTION

Below, the best mode for implementing the magnetic sensor of the present invention is described with reference to the drawings. In this embodiment, the description takes as an example of a magnetic sensor a biosensor used to detect biomolecules as the substance that is the target of detection, but this is intended to be illustrative and not limiting. The substance that is the target of detection and that can be detected by the magnetic sensor may include, besides biomolecules, various organic compounds or the like such as volatile organic compounds (VOCs) or the like included in contaminated water or the like.

Figure 1:
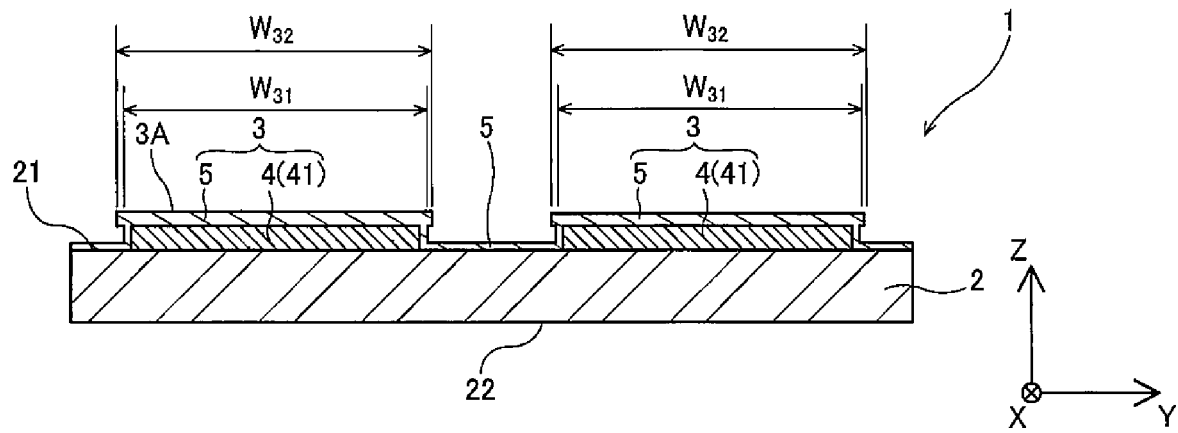
FIG. 1 is a cross-sectional view showing a schematic configuration of a first aspect of a biosensor according to an embodiment of the present invention.
Figure 2A:
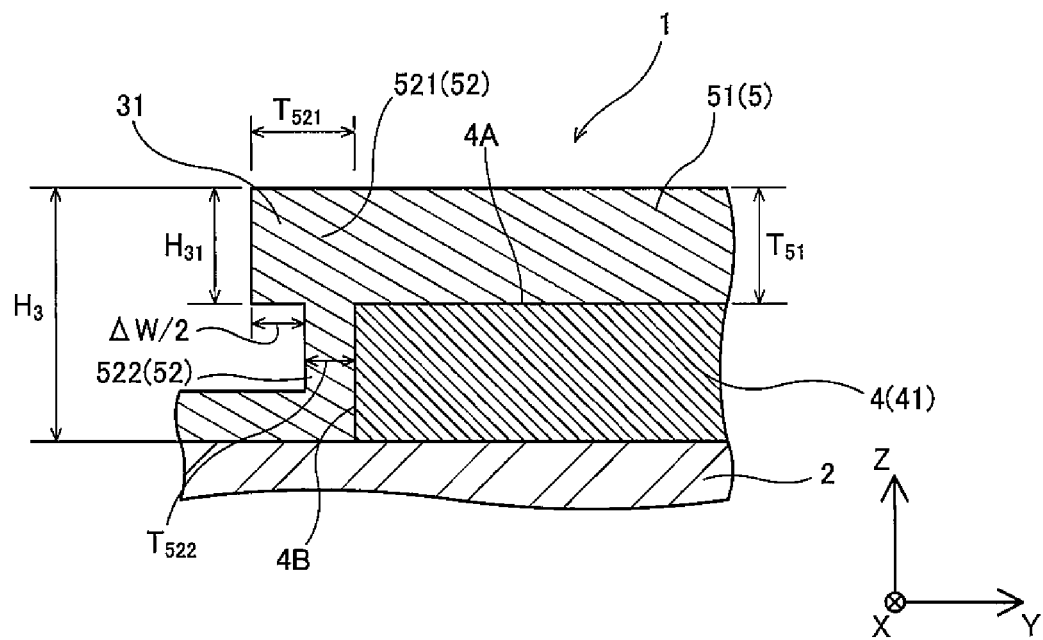
FIG. 2A is a partially enlarged cross-sectional view showing the first aspect of the biosensor according to the embodiment of the present invention.
Figure 2B:
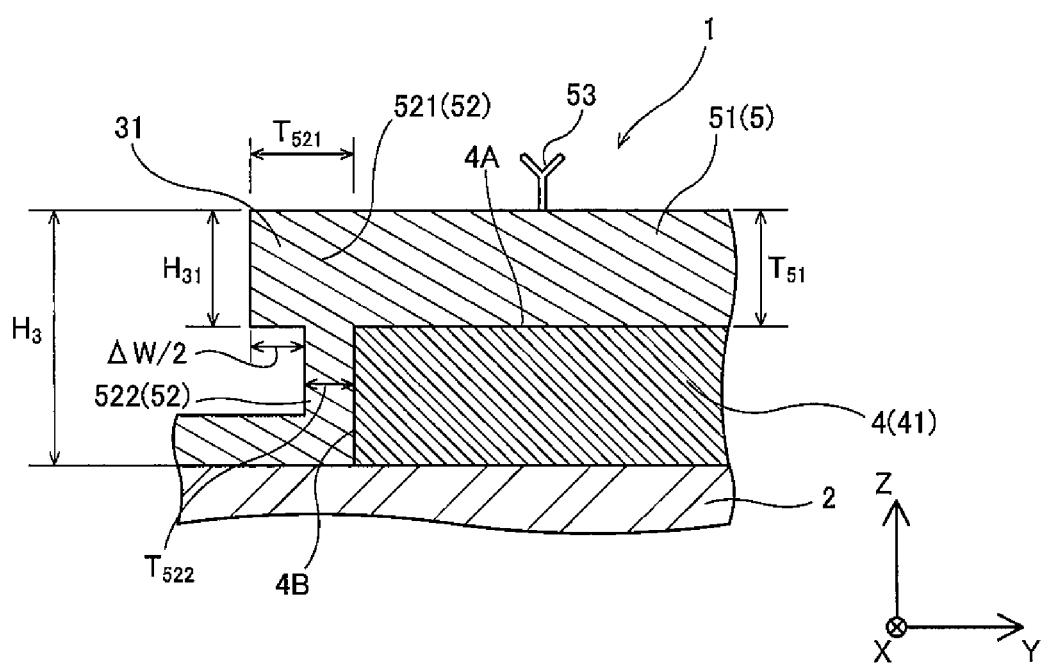
FIG. 2B is a partially enlarged cross-sectional view showing the first aspect of the biosensor according to the embodiment of the present invention.
Figure 3:
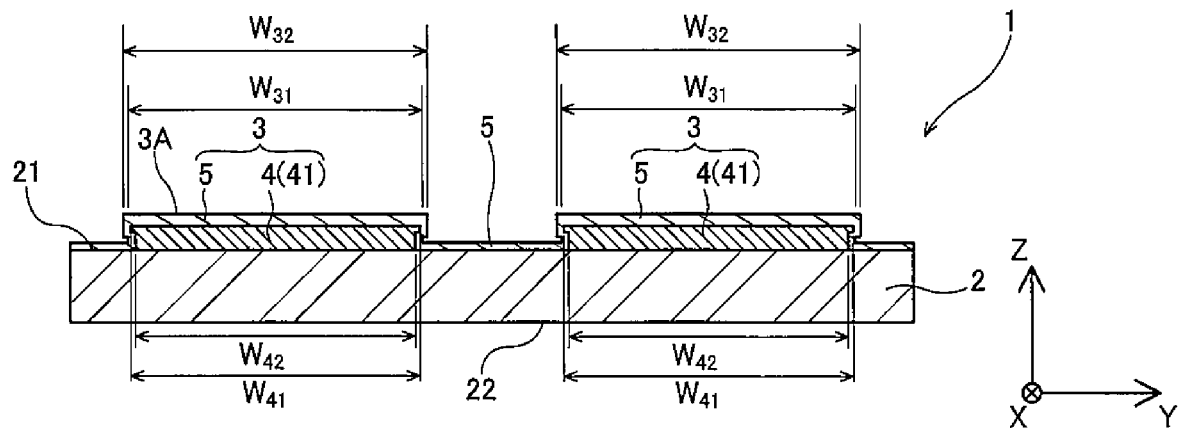
FIG. 3 is a cross-sectional view showing a schematic configuration of a second aspect of the biosensor according to the embodiment of the present invention.
Figure 4:
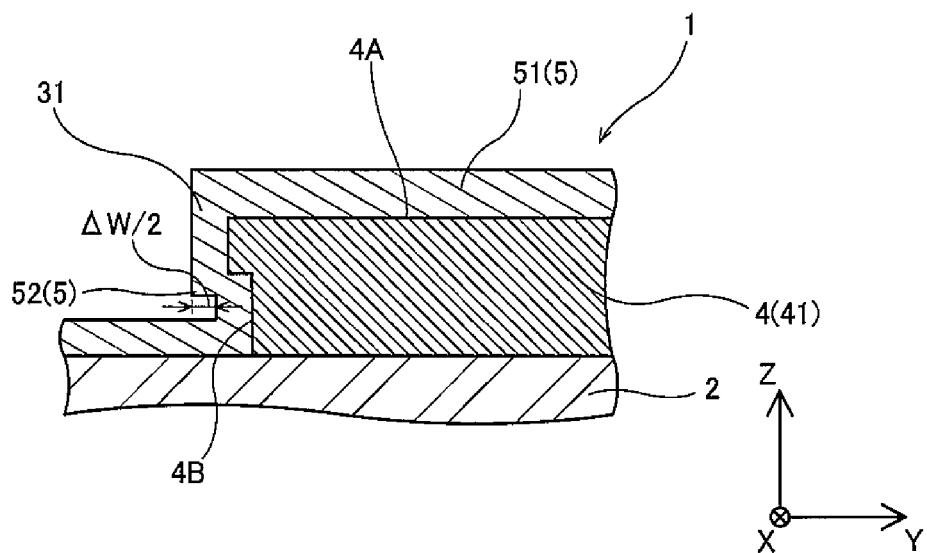
FIG. 4 is a partially enlarged cross-sectional view showing the second aspect of the biosensor according to the embodiment of the present invention.
Figure 5:
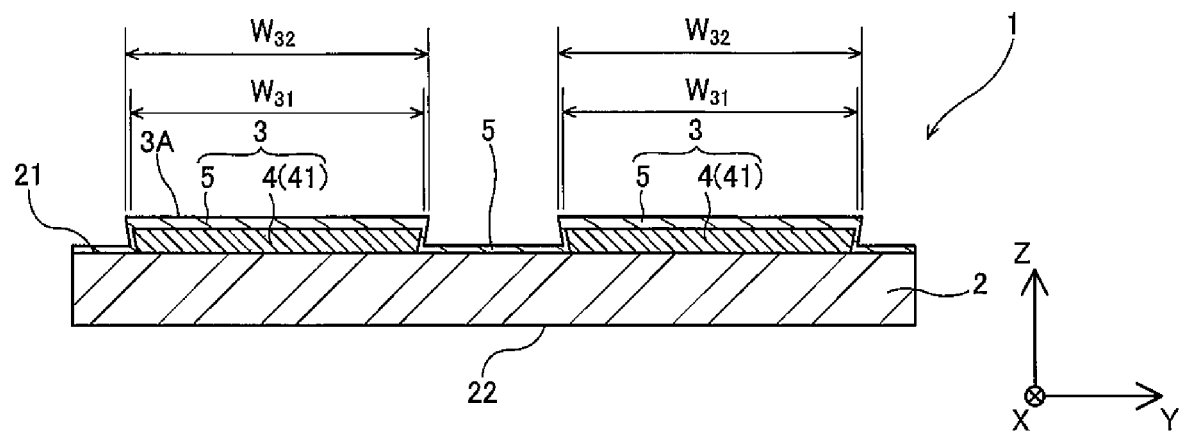
FIG. 5 is a cross-sectional view showing a schematic configuration of a third aspect of the biosensor according to the embodiment of the present invention.
Figure 6:
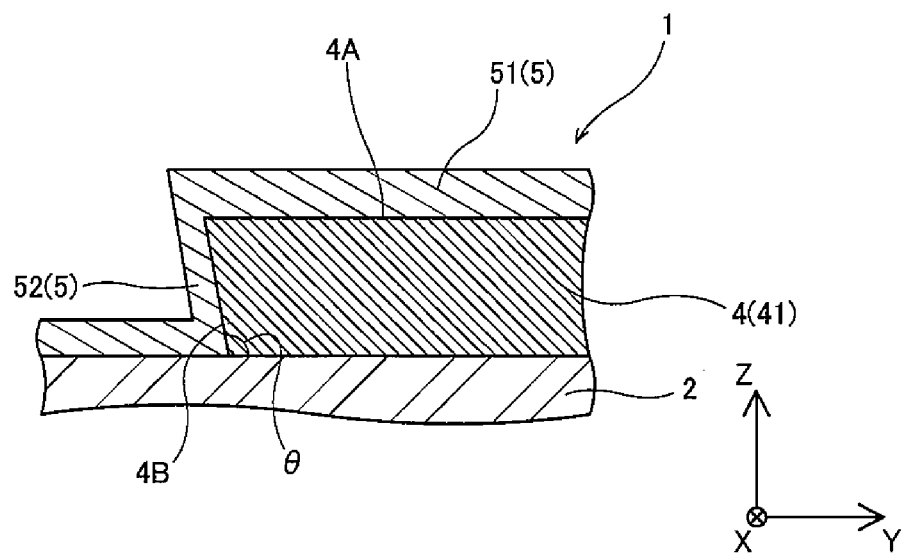
FIG. 6 is a partially enlarged cross-sectional view showing the third aspect of the biosensor according to the embodiment of the present invention.
Figure 7:
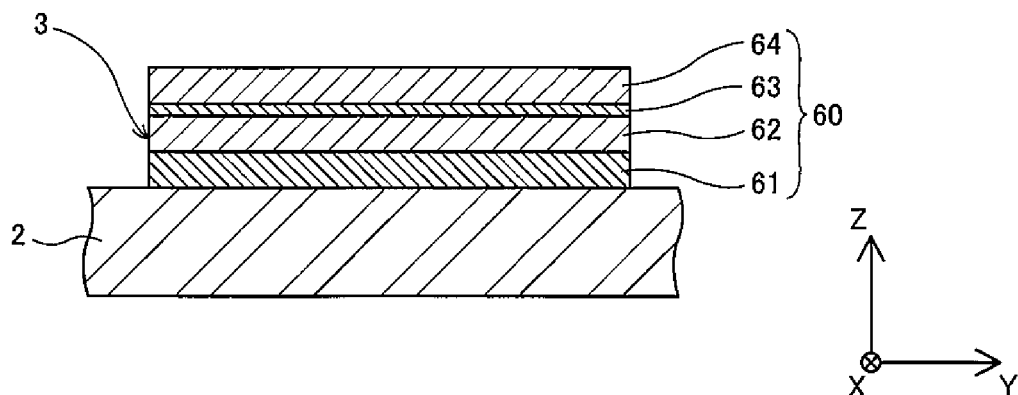
FIG. 7 is a cross-sectional view showing a schematic configuration of a magnetoresistive effect element according to the embodiment of the present invention.
Figure 8:
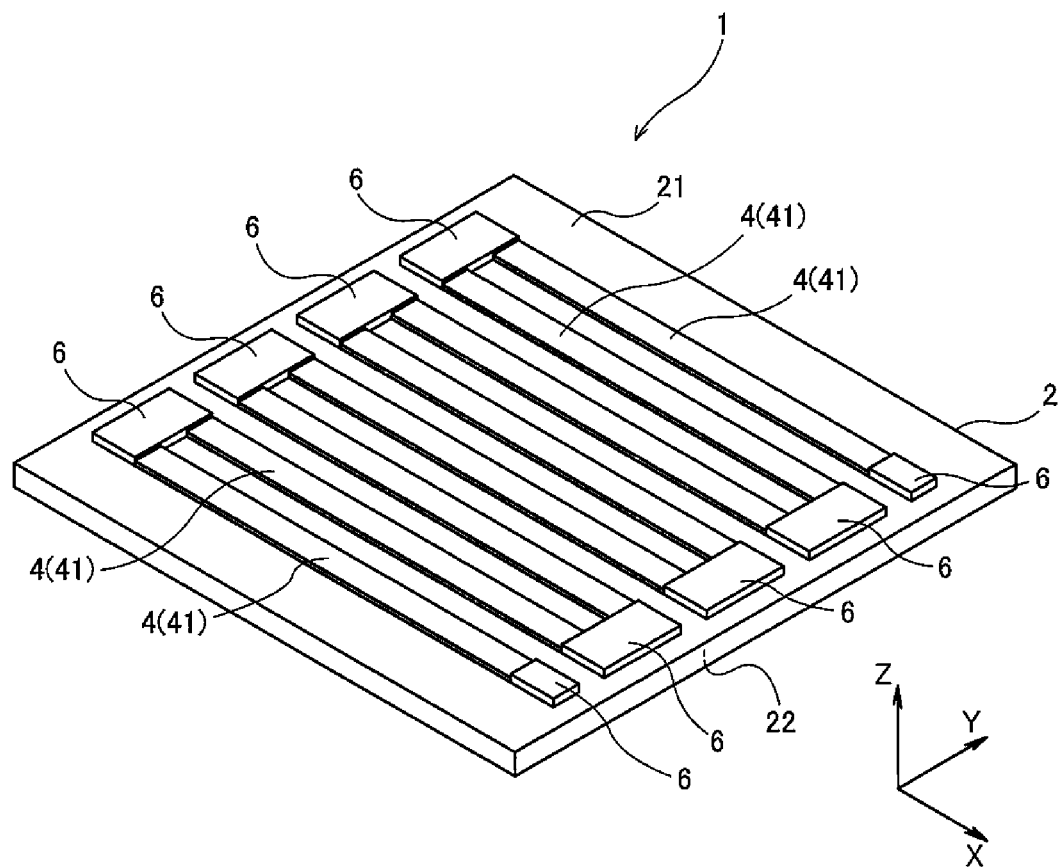
FIG. 8 is a perspective view showing a schematic configuration of the biosensor according to the embodiment of the present invention.

FIG. 1 is a cross-sectional view showing the schematic configuration of a first aspect of a biosensor according to this embodiment, FIGS. 2A and 2B are partially enlarged cross-sectional views showing the first aspect of the biosensor according to this embodiment, FIG. 3 is a cross-sectional view showing the schematic configuration of a second aspect of the biosensor according to this embodiment, FIG. 4 is a partially enlarged cross-sectional view showing the second aspect of the biosensor according to this embodiment, FIG. 5 is a cross-sectional view showing the schematic configuration of a third aspect of the biosensor according to this embodiment, FIG. 6 is a partially enlarged cross-sectional view showing the third aspect of the biosensor according to this embodiment, FIG. 7 is a cross-sectional view showing the schematic configuration of an magnetoresistive effect element according to this embodiment, and FIG. 8 is a perspective view showing the schematic configuration of the biosensor according to this embodiment.

In the biosensor according to this embodiment, an X direction, Y direction and Z direction are specified in some of the drawings, as necessary. Here, the X direction and the Y direction are directions orthogonal to each other within the plane of a substrate in this embodiment (within a plane substantially parallel to a first surface and a second surface of the substrate), and the Z direction is the direction of thickness of the substrate (the direction orthogonal to the first surface of the substrate).

As shown in FIGS. 1-6, a biosensor 1 according to this embodiment includes a substrate 2 having a first surface 21 and a second surface 22 opposite thereto, and a detection unit 3 provided on the first surface 21 of the substrate 2. The detection unit 3 comprises a magnetoresistive effect element 4 provided on the first surface 21 of the substrate 2, and a protective layer 5 that covers the top of the magnetoresistive effect element 4. The protective layer 5 includes a first protective layer 51 positioned on a top surface 4A of the magnetoresistive effect element 4, and a second protective layer 52 positioned on a side surface 4B of the magnetoresistive effect element 4. In the biosensor 1 according to this embodiment, by applying a magnetic field H on magnetic beads 10 that have accumulated biomolecules in a sample, captured in the protective layer 5 covering the magnetoresistive effect element 4, it is possible to detect the biomolecules by detecting with the magnetoresistive effect element 4 a stray magnetic field HS from the magnetic beads 10 (see FIG. 9).

The substrate 2 on which the magnetoresistive effect element 4 can be mounted can have a rectangular shape. Among those that can be used, for example, are a semiconductor substrate such as a silicon wafer or the like; a ceramic substrate such as AlTiC substrate, an alumina substrate or the like; a resin substrate; or a glass substrate or the like. An underlayer (omitted from the drawings) that includes $Al_2O_3$ or the like may be provided on the first surface 21 of the substrate 2 in accordance with the type of the substrate 2, and in particular between the first surface 21 of the substrate 2 and the magnetoresistive effect element 4. The thickness of the substrate 2 can be appropriately set from the perspectives of the strength of the substrate 2 and making the biosensor 1 light and thin but can be on the order of 5~100 nm, for example.

In this embodiment, a spin valve type of GMR element or the like can be used as the magnetoresistive effect element 4. As shown in FIG. 7, the magnetoresistive effect element 4 has an MR layered body 60 that includes an antiferromagnetic layer 61, a magnetization fixed layer 62, a nonmagnetic layer 63 and a free layer 64, layered in that order from the substrate 2 side. The antiferromagnetic layer 61 is composed of an antiferromagnetic material and serves the role of fixing the direction of magnetization of the magnetization fixed layer 62 by causing exchange coupling with the magnetization fixed layer 62. The magnetoresistive effect element 4 may have a configuration in which the free layer 64, the nonmagnetic layer 63, the magnetization fixed layer 62 and the antiferromagnetic layer 61 are layered in that order from the substrate 2 side. In addition, the antiferromagnetic layer 61 may be omitted by the magnetization fixed layer 62 being a so-called self-pinned fixed layer (Synthetic Ferri Pinned layer, or SFP layer) having a layered ferri structure of a ferromagnetic layer/nonmagnetic intermediate layer/ferromagnetic layer and both ferromagnetic layers being antiferromagnetically coupled.

In the GMR element as the magnetoresistive effect element 4, the nonmagnetic layer 63 is a nonmagnetic conductive layer. In the GMR element, the resistance value changes in accordance with the angle formed by the direction of magnetization of the free layer 64 with respect to the direction of magnetization of the magnetization fixed layer 62, and the resistance value is a minimum when this angle is 0° (when the magnetization directions are parallel to each other) and the resistance value is a maximum when this angle is 180° (when the magnetization directions are antiparallel to each other).

As shown in FIG. 8, the magnetoresistive effect element 4 includes a plurality of linear sections 41 extending along the X direction (first direction). The linear sections 41 are arranged with prescribed gaps in the Y direction (second direction) and are configured in a meandering shape by the ends of adjacent linear sections 41 (ends in the X direction (first direction)) being connected by lead electrodes 6. In FIG. 8, depiction of the protective layer 5 has been omitted because such would make the drawing complicated.

A GMR element as the magnetoresistive effect element 4 in general has a relatively low element resistance value, so to cause a signal of prescribed strength to be output from the biosensor 1, it is necessary to make the line width of the GMR element narrow and the line length long. By configuring the GMR element in the above-described meandering shape, it is possible to make the line width of the GMR element narrow and the line length long within a limited region on the first surface 21 of the substrate 2. The lead electrodes 6 can be made of one of the electroconductive materials Cu, Al, Au, Ta, Ti or the like, for example, or a composite film of two or more electroconductive materials.

In the magnetoresistive effect element 4 composed of the above-described plurality of linear sections 41, the magnetization direction of the magnetization fixed layer 62 is substantially parallel to the short direction of each linear section 41 (Y direction, second direction). In the biosensor 1 according to this embodiment, by applying a magnetic field H in a direction orthogonal to the first surface 21 of the substrate 2 on the magnetic beads 10 captured in the protective layer 5 on the magnetoresistive effect element 4, a stray magnetic field $H_s$ is generated from the magnetic beads 10 and applied on the magnetoresistive effect element 4 (see FIG. 9). By this stray magnetic field HS being applied on the magnetoresistive effect element 4, the direction of magnetization of the free layer 64 changes and through this the resistance value of the magnetoresistive effect element 4 changes. By this change in resistance value being output as a signal, the existence of and quantity of biomolecules in the sample can be detected in the biosensor 1.

The length of the linear sections 41 in the lengthwise direction can be appropriately established in accordance with the size of the biosensor 1 as a whole and the sensitivity required of the biosensor 1, but for example can be on the order of 10~500 µm, and the length in the short direction can be on the order of 0.2~10 µm, for example.

As shown in FIGS. 1-6, when the cross-section along the Y direction (second direction) of the biosensor 1 according to this embodiment is viewed, the detection unit 3 has a first width $W_{31}$ and a second width $W_{32}$. The first width $W_{31}$ is the length of the detection unit 3 on the first surface 21 of the substrate 2 (the length along the Y direction (second direction)), and the second width $W_{32}$ is the length of a top surface 3A of the detection unit 3 (surface positioned upward (+Z side) from the first width $W_{31}$) (the length along the Y direction (second direction)). The first width $W_{31}$ is the sum of a width $W_{41}$ of the magnetoresistive effect element 4 (linear sections 41) on the first surface 21 of the substrate and the thicknesses $T_{522}$ and $T_{522}$ of the second protective layers 52 and 52 positioned on both side surfaces 4B and 4B of the magnetoresistive effect element 4.

The second width $W_{32}$ of the detection unit 3 is preferably larger than the first width $W_{31}$. By having the second width $W_{32}$ be larger than the first width $W_{31}$, it is possible to detect with high accuracy the biomolecules that are the detection target substance using the magnetic beads 10. The difference between the first width $W_{31}$ and the second width $W_{32}$ ($W_{32}-W_{31}$) can be on the order of 2.0 nm or greater and can be on the order of 2.0~60.0 nm.

When a cross-section along the Y direction (second direction) of the biosensor 1 according to this embodiment is viewed, the detection unit 3 having the second width $W_{32}$ larger than the first width $W_{31}$ may have a protruding part 31 that protrudes in the Y direction (second direction) near the top surface 3A of the detection unit 3. In the first aspect shown in FIG. 1 and FIG. 2A, when the cross-section along the Y direction (second direction) is viewed, the height $H_{31}$ of the protruding part 31 can be on the order of not more than ⅔ of the height $H_3$ of the detection unit 3 (the length along the Z direction (third direction) from the first surface 21 of the substrate 2 to the top surface 3A of the detection unit 3) and is preferably on the order of 1~60.0 nm. When the height $H_{31}$ of the protruding part 31 exceeds ⅔ of the height $H_3$ of the detection unit 3, the protective layer 5 becomes thick on the top surface 4A of the magnetoresistive effect element 4 and the distance between the magnetoresistive effect element 4 and the magnetic beads 10 (see FIG. 9) captured in the protective layer 5 becomes large, it may be difficult for the stray magnetic field $H_s$ generated from the magnetic beads 10 to be appropriately applied on the magnetoresistive effect element 4. The protrusion length $\Delta W/2$ of the protruding part 31 can be on the order of 1.0~30.0 nm, for example, and is preferably on the order of 2.0~15.0 nm. When this protrusion length $\Delta W/2$ is less than 1.0 nm, it is difficult to capture the magnetic beads 10 (see FIG. 9) in the second protective layer 52 positioned on the side surfaces 4B and 4B of the magnetoresistive effect element 4 (linear sections 41), so the detection accuracy in the biosensor 1 may decrease. On the other hand, when the protrusion length $\Delta W/2$ of the protruding part 31 exceeds 30.0 nm, the thickness $T_{522}$ of the second protective layer 52 positioned at both side surfaces 4B and 4B of the magnetoresistive effect element 4 (linear sections 41) may become too thin. As described below, the biosensor 1 is used by being caused to infiltrate a sample 200 (a solution) (see FIG. 11), but when the protrusion length $\Delta W/2$ of the protruding part 31 exceeds 30.0 nm and the thickness $T_{522}$ of the second protective layer 52 becomes too thin, the sample 200 (solution) makes contact with the magnetoresistive effect element 4 (linear sections 41), and resistance anomalies may arise in the magnetoresistive effect element 4 (linear sections 41) and the detection accuracy of the biosensor 1 may decrease. As a detection unit 3 having the protruding part 31, a portion of the top side (+Z side) of the second protective layer 52 may protrude in the Y direction (second direction) (see FIG. 2A), or a portion of the top surface 4A side of the magnetoresistive effect element 4 may protrude in the Y direction (second direction) (see FIG. 4). The detection unit 3 can have a second width $W_{32}$ that is larger than the first width $W_{31}$, and as shown in FIG. 5 and FIG. 6, when the cross-section along the Y direction (second direction) is viewed, the detection unit 3 may also have an inverted taper shape.

In the first aspect shown in FIG. 2A, the thickness $T_{521}$ of the second protective layer 52 on the upward side (+Z side) can be greater than the thickness $T_{522}$ of the second protective layer 52 on the first surface 21 of the substrate 2, and the ratio of the thickness $T_{521}$ to the thickness $T_{522}$ is preferably 1:0.05~1:0.95, and more preferably 1:0.1~1:0.9, and still more preferably 1:0.5~1:0.8. When the ratio of the thickness $T_{521}$ and the thickness $T_{522}$ is outside the above-described range, it is difficult for the magnetic beads 10 to be captured in the protective layer 5 via biomolecules, so biomolecule detection accuracy may decrease.

In the second aspect shown in FIG. 4, the width $W_{41}$ of the magnetoresistive effect element 4 on the upward side (+Z side) can be larger than the width $W_{42}$ of the magnetoresistive effect element 4 on the first surface 21 side of the substrate 2, and the difference between the width $W_{41}$ and the width $W_{42}$ can be on the order of 1.0 nm or more, and is preferably 1.0~60.0 nm, and more preferably 2.0~40.0 nm, and still more preferably 4.0~30.0 nm. When the difference between the width $W_{41}$ and the width $W_{42}$ is less than 1 nm, the protective layer 5 covering the magnetoresistive effect element 4, in particular the second protective layer 52 positioned on the side surface 4B of the magnetoresistive effect element 4, may be discontinuous, and the sample 200 (solution) may contact the magnetoresistive effect element 4 (linear sections 41) and the magnetoresistive effect element 4 (linear sections 41) may be etched, resistance anomalies may arise and the detection accuracy of the biosensor 1 may decrease. In addition, when the difference between the width $W_{41}$ and the width $W_{42}$ exceeds 60.0 nm, shape anisotropy of the free layer and the magnetization fixed layer is expressed, the execution area of the magnetoresistive effect element 4 diminishes, and the region where the stray magnetic field $H_s$ generated from the magnetic beads 10 cannot be properly detected expands, so biomolecule detection accuracy may decrease.

When the cross-section along the Y direction (second direction) of the biosensor 1 according to this embodiment is viewed, the thickness $T_{51}$ of the first protective layer 51 can be thicker than the thickness $T_{521}$ of the second protective layer 52 on the upward side (+Z side), and the ratio of the thickness $T_{51}$ to the thickness $T_{521}$ is preferably 1:0.5~1:1, and more preferably 1:0.1~1:0.95, and still more preferably 1:0.2~1:0.5. When the ratio of the thickness $T_{51}$ to the thickness $T_{521}$ is outside the above-described range, removing the magnetic beads 10 captured in the protective layer 5 becomes difficult, so the detection accuracy of the biosensor 1 may decrease.

In this embodiment, the angle θ of the side surface 4B of the magnetoresistive effect element 4 with respect to the first surface 21 of the substrate 2 is preferably 90~135°, and more preferably 95~100°. By having this angle θ within the above-described range, the first protective layer 51 can be relatively easily formed as a thick film above both side surfaces 4B and 4B of the magnetoresistive effect element 4 (linear sections 41) and the second protective layer 52 can be relatively easily formed as a thin film below both side surfaces 4B and 4B, so process management of the protrusion length $\Delta W/2$ of the protruding part 31 becomes easy. As a result, it is possible to make the second width $W_{32}$ of the detection unit 3 larger than the first width $W_{31}$.

In this embodiment, the protective layer 5 that covers the entirety of the magnetoresistive effect element 4 and the first surface 21 of the substrate 2 is a layer in which biomolecules accumulated on the magnetic beads 10 can be captured. The biomolecules accumulated on the magnetic beads 10 may be captured on the protective layer 5 though an electrostatic interaction, a hydrogen bonding interaction or the like with the protective layer 5 or may be captured by a probe 53 (see FIG. 2B) provided on the surface of the protective layer 5 and capable of bonding specifically with the biomolecules. The protective layer 5 may be made of a material that can exert an electrostatic interaction, a hydrogen bonding interaction or the like with a biomolecule, such as $SiO_2$, $Al_2O_3$, $Si_3N_4$, TiN, TaN, TaO, TiO, AlN or the like, for example. To make it possible to easily capture biomolecules on the surface of the protective layer 5, a material with an affinity capable of bonding specifically with the biomolecules that are the target of detection may be provided. The protective layer 5 may have a single-layer structure with one layer made of the above-described material or may have a multi-layer structure with two or more layers. When the protective layer 5 is a multi-layer structure, the material composing each of the layers of this multi-layer structure may be the same material or may be differing materials. When the protective layer 5 has a multi-layer structure, for example when the protective layer 5 is formed through sputtering in the process of manufacturing the biosensor 1 shown in FIG. 1 and FIG. 2A, by adjusting the processing conditions in sputtering (for example, the film formation temperature, the discharge power and film formation pressure, the distance between the target and the film formation target, and the like), control of the film formation rate on the top surface of the magnetoresistive effect element 4 and the film formation rate on the side surfaces becomes possible, and it is possible to adjust the protrusion amount of the protective layer 5 on the side surfaces of the magnetoresistive effect element 4. As a result, it is possible to make the second width $W_{32}$ of the detection unit 3 larger than the first width $W_{31}$.

The thickness $T_{51}$ of the first protective layer 51 positioned above the magnetoresistive effect element 4 is for example set to around 3~200 nm. When the protective layer 5 has a multi-layer structure, the thickness of each layer can be on the order of 0.1~100 nm, for example. For the second protective layer 52, the thickness $T_{521}$ of the second protective layer 52 on the upward side (+Z side) can be within the range of 2~60 nm, for example, and the thickness $T_{522}$ of the second protective layer 52 on the substrate 2 side (−Z side) can be within the range of 1~59 nm, for example.

By causing the biosensor 1 having the above-described configuration to contact a sample that includes biomolecules 11 that are the target of detection, it is possible to cause the biomolecules 11 to be captured on the surface of the protective layer 5. Furthermore, after the magnetic beads 10 and the biomolecules 11 captured on the surface of the protective layer 5 are caused to bond, the magnetic beads 10 and the biomolecules 11 that were not captured on the surface of the protective layer 5 on the magnetoresistive effect element 4 can be selectively removed through a gradient magnetic field or washing or the like. In this embodiment, by having the second width $W_{32}$ of the detection unit 3 be larger than the first width $W_{31}$, it is possible to facilitate capturing the biomolecules 11 and the magnetic beads 10 on the protective layer 5, particularly in the second protective layer 52 formed on the side surfaces of the detection unit 3, and it is possible to make removal of the captured biomolecules 11 and magnetic beads 10 difficult through applying a gradient magnetic field, or washing, or the like. Through this, it is possible to detect the existence of and the quantity of biomolecules with high accuracy using the magnetic beads 10, and it is possible to control variation in detection results.

Figure 9:
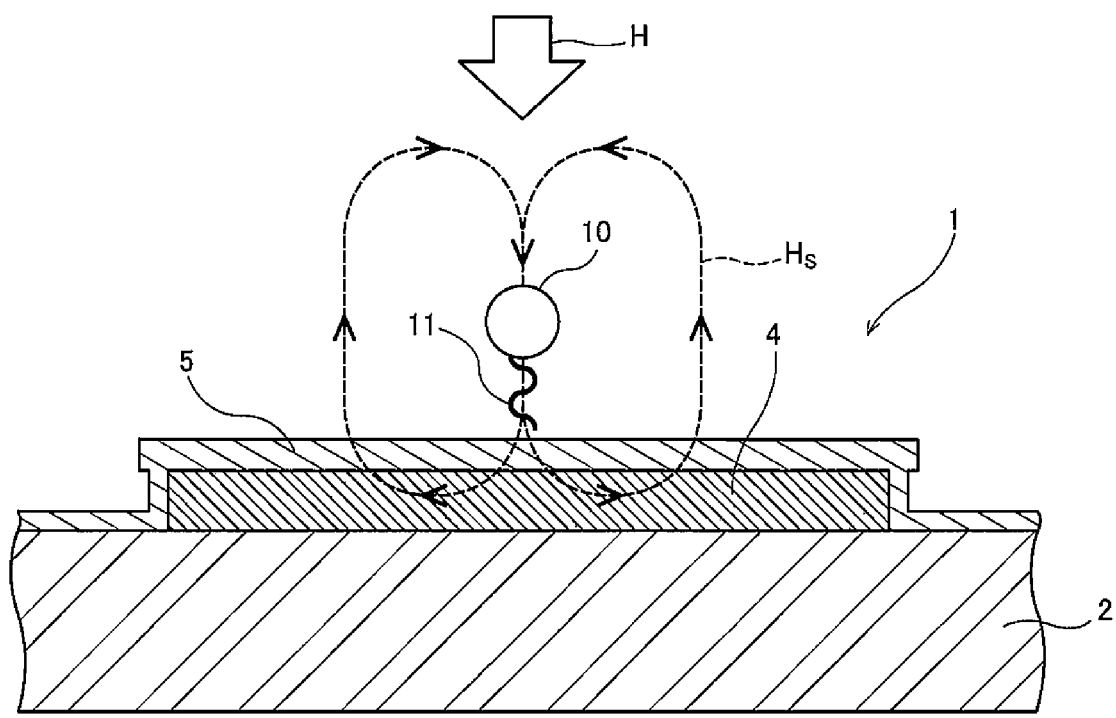
FIG. 9 is a cross-sectional view for describing an overview of a biomolecule detection method using the biosensor according to the embodiment of the present invention.

As described above, after the biomolecules 11 and the magnetic beads 10 are left on the surface of the protective layer 5 on the magnetoresistive effect element 4, by applying a magnetic field H in a direction orthogonal to the first surface 21 of the substrate 2, the magnetic beads 10 take on magnetism and the stray magnetic field $H_s$ is generated from the magnetic beads 10 (see FIG. 9). By this stray magnetic field $H_s$ being applied on the magnetoresistive effect element 4, the magnetization direction of the free layer 64 changes. As a result, the resistance value of the magnetoresistive effect element 4 changes. This resistance value change has a correlation (linear correlation) with the number of magnetic beads 10 bonded to the biomolecules 11 captured on the surface of the protective layer 5, so by this resistance value change being output from the biosensor 1 as a signal, it is possible to detect the existence of and the quantity of biomolecules that are the detection target in the sample.

As the biomolecules 11 that can be detected using the biosensor 1 according to this embodiment, the following can be listed, for example: nucleic acids such as DNA, mRNA, miRNA, siRNA, artificial nucleic acids (for example, Locked Nucleic Acid (LNA), Bridged Nucleic Acid (BNA) or the like) or the like (these may be naturally derived or chemically synthesized); peptides such as ligands, cytokines, hormones or the like; proteins such as receptors, enzymes, antigens, antibodies or the like; or cells, viruses, bacteria, fungi or the like.

In addition, as samples containing the biomolecules 11 that are the detection target, the following can be listed, for example: blood, blood serum, blood plasma, urine, puffy coat, saliva, semen, pleural effusion, cerebrospinal fluid, tears, sputum, mucus, lymph, abdominal fluid, etc. Examples include pleural effusion, amniotic fluid, bladder lavage fluid, bronchial alveolar lavage fluid, cell extract fluid, cell culture supernatants and the like.

The magnetic beads can be particles that can be magnetized and, for example, can be particles or the like made of gold, iron oxide or the like. The average particle diameter of the magnetic beads 10 can be on the order of 5~250 nm, for example, and preferably on the order of 20~150 μm. The average particle diameter of the magnetic beads 10 can, for example, be measured using a laser diffraction-type particle diameter distribution measurement device (product name: SALD-2300, made by Shimadzu Corp.).

The surface of the magnetic beads 10 may have fixed thereto a protein such as streptavidin or the like and may be further provided with an affinity substance capable of bonding specifically with the biomolecules. When used to capture ligands as the biomolecules 11, the magnetic beads 10 preferably have a hydrophilic surface, and when used to capture antibodies as the biomolecules 11, the magnetic beads 10 preferably have a hydrophobic surface.

With the biosensor 1 having the above-described configuration, by making the second width $W_{32}$ of the detection unit 3 larger than the first width $W_{31}$, it is possible to facilitate capturing the biomolecules 11 and the magnetic beads 10 on the protective layer 5, and it is possible to make removal of the captured biomolecules 11 and magnetic beads 10 difficult through applying a gradient magnetic field, or washing, or the like. With the biosensor 1 according to this embodiment, it is possible to detect the existence of and the quantity of biomolecules with high accuracy using the magnetic beads 10, and it is possible to control variation in detection results.

The biosensor 1 having the above-described configuration can, for example, be produced as follows. FIGS. 10A~10E are process flow diagrams showing in cross-sectional view the procedures of the method of manufacturing the biosensor 1 according to this embodiment.

Figure 10A:
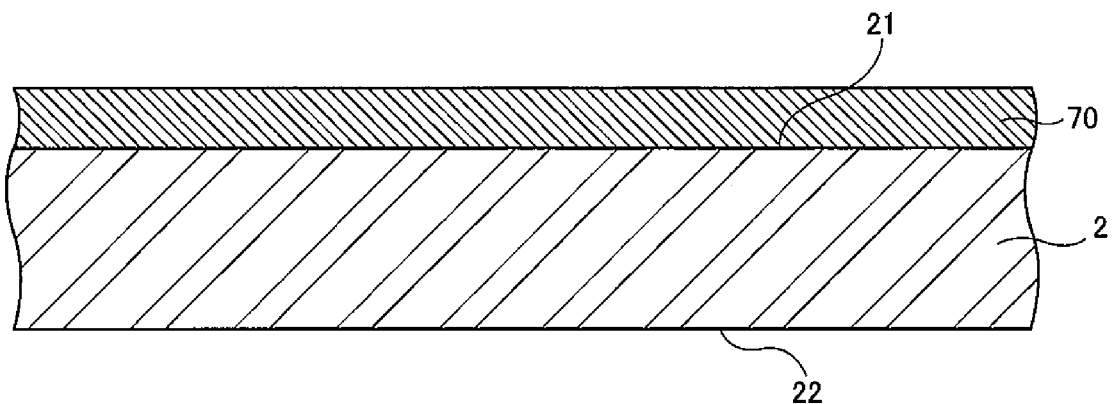
FIG. 10A is a cross-sectional view showing one step of the manufacturing process for the second aspect of the biosensor according to the embodiment of the present invention.
Figure 10B:
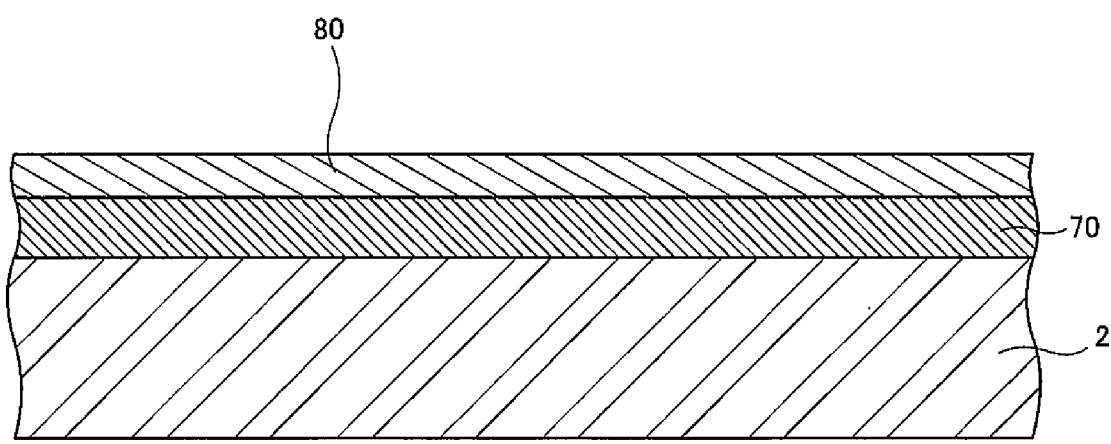
FIG. 10B is a cross-sectional view showing the step following the step shown in FIG. 10A.

An underlayer (omitted from drawings) that includes $Al_2O_3$ or the like is formed on a planned region that forms the magnetoresistive effect element 4 on the first surface 21 of the substrate 2, being a semiconductor substrate such as a silicon wafer or the like, a ceramic substrate such as an AlTiC substrate, an alumina substrate or the like; a resin substrate; or a glass substrate or the like, and an MR film 70 (a layered film with an antiferromagnetic film, a ferromagnetic film, a nonmagnetic film and a ferromagnetic film layered in that order) is formed through sputtering or the like on the first surface 21 of the substrate 2 (see FIG. 10A).

Figure 10C:
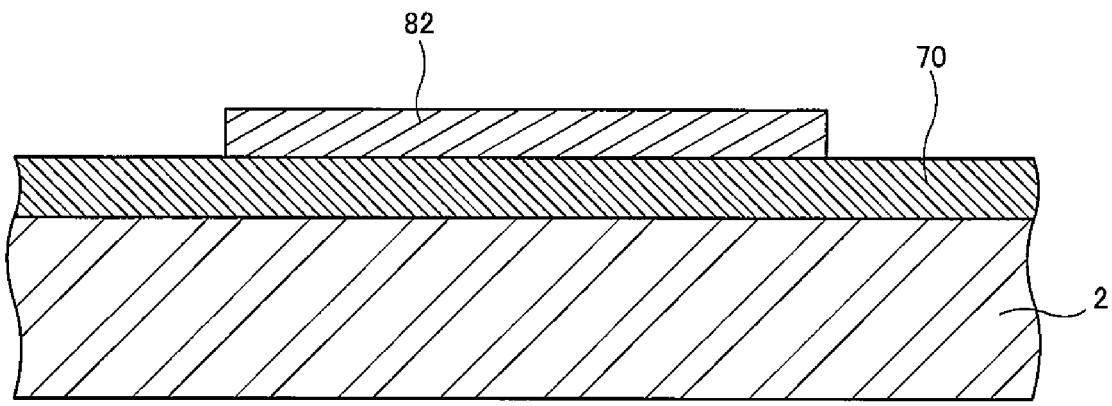
FIG. 10O is a cross-sectional view showing the step following the step shown in FIG. 10B.
FIG. 10D is a cross-sectional view showing the step following the step shown in FIG. 10C.
FIG. 10E is a cross-sectional view showing the step following the step shown in FIG. 10D.

Next, a resist layer 80 covering the MR film 70 is formed (see FIG. 10B), and through an exposure/development process, a resist pattern 82 is formed, corresponding to the magnetoresistive effect element 4 (see FIG. 10C). As the resist material that makes up the resist layer 80, a positive type or a negative type may be used, and a cyclopentanone-class resist material, a Novolac resin-class resist material or the like can be cited.

Figure 10D:
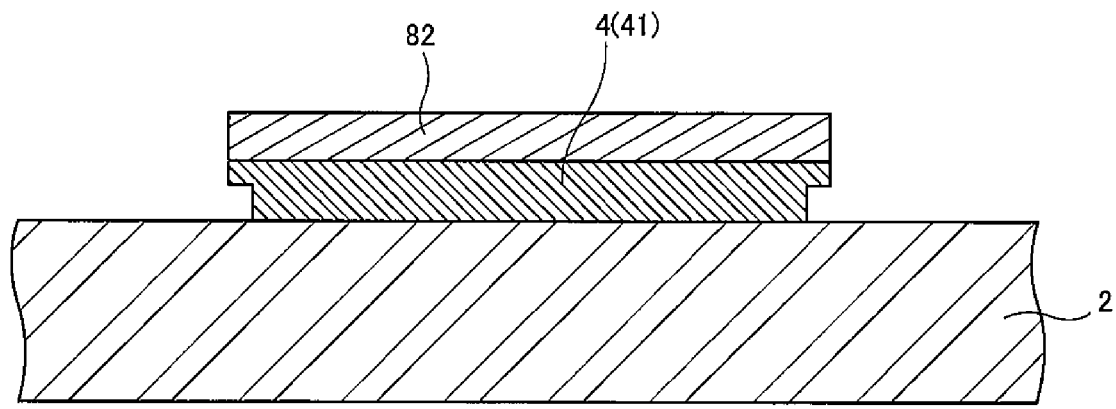
Figure 10E:
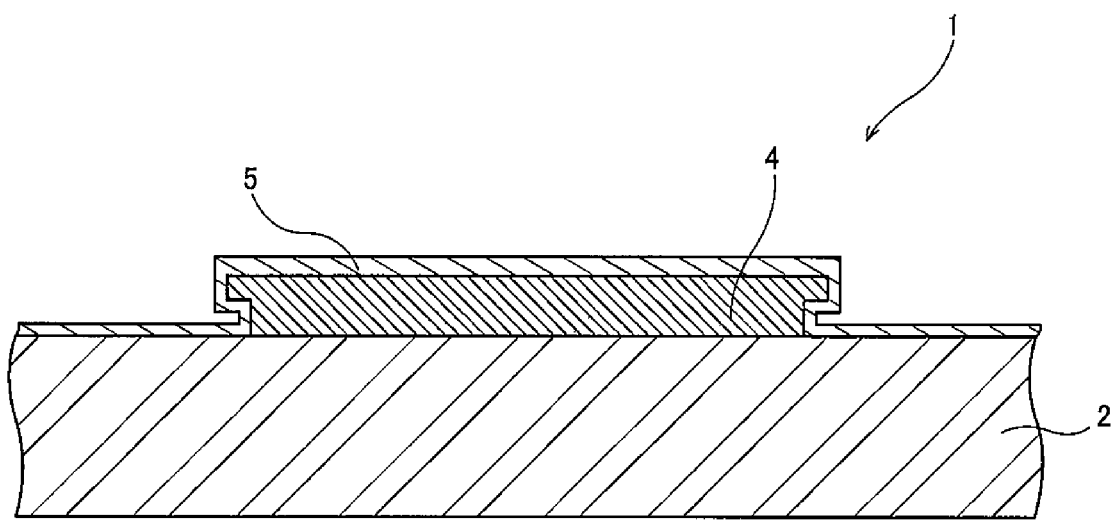

Next, the MR film 70 undergoes a milling process with the resist pattern 82 as a mask (see FIG. 10D). As the milling process, a process can be used, for example, in which an ion beam is incident on the MR film 70 and the part of the MR film 70 on which the ion beam is incident is removed. The MR film 70 that is removed in this milling process is caused to be redeposited on the side surfaces 4B of the linear sections 41 formed through this milling process. This way, it is possible to make the second width $W_{32}$ of the detection unit 3 larger than the first width $W_{31}$. To cause redeposition of the MR film 70 on the side surfaces 4B of the linear sections 41, it is possible to use a method in which the angle of incidence of the ion beam in the million process is caused to be substantially orthogonal to the MR film 70. The angle of incidence of the ion beam being substantially orthogonal to the MR film 70 means that the angle is orthogonal to the extent that the MR film 70 is deposited on the side surfaces 4B of the linear sections 41, and the angle of incidence can be within the range of 65~85°, for example. The angle of incidence of the ion beam means the angle formed by the direction of incidence of the ion beam and the first surface 21 of the substrate 2. To control the protrusion amount of the protruding part 31 of the detection unit 3, the angle of incidence of the ion beam may be caused to fluctuate while the MR film 70 is being removed, for example. For example, by causing the angle of incidence of the ion beam to be orthogonal to the MR film 70 while the MR film 70 is being removed, when there is excess redeposition on the side surfaces 4B of the linear sections 41 and the protrusion amount of the protruding part 31 becomes too large, the angle of incidence of the ion beam may be adjusted to a value deviating from the above-described numerical range during the milling process on the MR film 70. Accordingly, it is possible to control the protrusion length ΔW/2 of the protruding part 31 of the detection unit 3 to the range desired.

Next, by applying a magnetic field while implementing a prescribed annealing process, the magnetoresistive effect element 4, which includes the plurality of linear sections 41, is formed on the first surface of the substrate 2. The applied magnetic field can be appropriately set so that a prescribed exchange magnetic anisotropy is induced between the antiferromagnetic layer 61 and the magnetization fixed layer 62 in accordance with the effective vertical magnetic anisotropic energy Keff or the like given from the vertical magnetic anisotropic energy Ku and the shape anisotropic energy Kd of the magnetization fixed layer 62, the constituent materials of each layer and the film thickness, dimensions and shape of each layer of the magnetoresistive effect element 4.

Next, by forming the lead electrodes 6 that connect the ends of adjacent linear sections 41 in the lengthwise direction through sputtering or the like of electroconductive materials, the magnetoresistive effect element 4 is formed. In addition, after the resist pattern 82 has been removed, the protective layer 5 that covers the first surface 21 of the substrate 2 and the magnetoresistive effect element 4 is formed by a CVD method, a PVD method such as reactive sputtering or the like, or a film formation method such as a vacuum deposition method or the like (see FIG. 10E). In this manner, it is possible to manufacture the biosensor 1 according to this embodiment.

Figure 11:
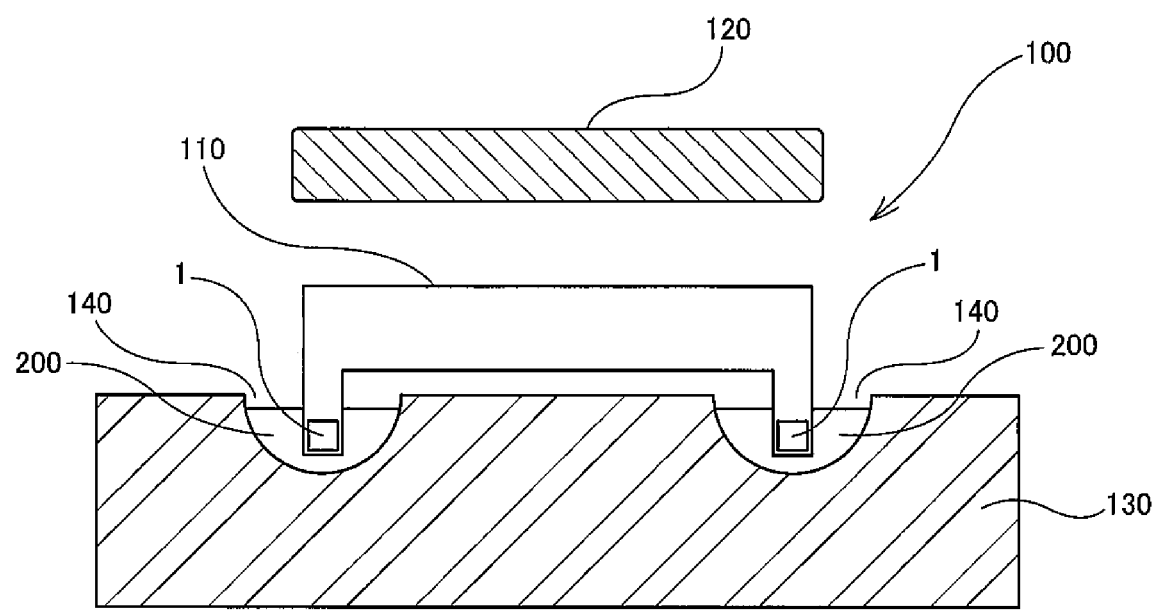
FIG. 11 is a cross-sectional view showing the schematic configuration of a magnetic detection system according to the embodiment of the present invention.

A magnetic detection device using the biosensor 1 having the above-described configuration and a magnetic detection system provided with this magnetic detection device will be described. FIG. 11 is a cross-sectional view showing the schematic configuration of a magnetic detection system according to this embodiment.

A magnetic detection system 100 in this embodiment is provided with a magnetic detection device having the biosensor 1 and a support unit 110 that supports this biosensor 1, a magnetic field generation unit 120 and a plate 130 having a plurality of reservoirs 140 that hold a sample 200 containing biomolecules.

A probe 53 (for example, a ligand or the like) that can bond specifically with the biomolecules in the sample 200 may be provided on the surface of the protective layer 5 of the biosensor 1 (see FIG. 2B). Of course, the surface of the protective layer 5 of the biosensor 1 may also be configured so that the biomolecules are captured on the protective layer 5 by electrostatic interaction, hydrogen bonding interaction or the like, without the probe 53 being provided on the surface of the protective layer 5 of the biosensor 1. The biomolecules in the sample 200 can be accumulated on the magnetic beads 10 (see FIG. 9). The support unit 110 that supports the biosensor 1 has a plurality of strip-shaped sections of a size capable of being inserted into the reservoirs 140, respectively. When the tips of the strip-shaped sections are inserted into the reservoirs 140 the biosensor 1 is attached to the tip of each strip-shaped section so that the biosensor 1 is caused to contact the sample 200 housed in each reservoir 140. The support unit 110 is provided to be capable of raising and lowering. Accordingly, it is possible to insert each of the strip-shaped sections into each of the reservoirs 140 and to remove such from each of the reservoirs 140.

The magnetic field generation unit 120 comprises coils or the like that can generate a magnetic field in a direction orthogonal to the first surface 21 of the substrate 2 of the biosensor 1, for example, and is provided so that a magnetic field can be applied on the biosensor 1 when the biosensor 1 is caused to contact the sample 200 housed in each reservoir 140.

In the magnetic detection system 100 having this kind of configuration, when the biosensor 1 is caused to contact the sample 200 housed in each of the reservoirs 140, the biomolecules accumulated on the magnetic beads 10 (see FIG. 9) are captured on the protective layer 5 of the biosensor 1. In this state, when a magnetic field is generated in a direction orthogonal to the first surface 21 of the substrate 2 from the magnetic field generation unit 120, the magnetic beads 10 take on magnetism and the stray magnetic field HS (see FIG. 9) is generated from the magnetic beads 10. By this stray magnetic field HS being applied on the magnetoresistive effect element 4, the magnetization direction of the free layer 64 changes. As a result, the resistance value of the magnetoresistive effect element 4 changes and a signal is output from the biosensor 1. The change in resistance value of the magnetoresistive effect element 4 has a correlation (linear correlation) with the number of magnetic beads 10 bonded to the biomolecules 11 captured on the surface of the protective layer 5, so in the magnetic detection system 100, the existence of and quantity of the biomolecules in the sample can be detected based on the signal output from the biosensor 1.

In the above-described magnetic detection system 100, the magnetic field generation unit 120 generates a magnetic field to magnetize the magnetic beads 10. In a state in which the biomolecules accumulated on the magnetic beads 10 are captured on the protective layer 5 of the biosensor 1, an alternating current magnetic field may be caused to be generated in the in-plane direction (the in-plane direction of the XY plane) of the magnetoresistive effect element 4. In the magnetic detection system 100 of this aspect, first, the biosensor 1 is caused to contact the sample 200 contained in each of the reservoirs 140, the magnetic beads 10 are magnetized by the magnetic field generated from the magnetic field generation unit 120, and the biomolecules accumulated on the magnetized magnetic beads 10 are captured on the protective layer 5 of the biosensor 1. In this state, when the alternating current magnetic field is caused to be generated from the magnetic field generation unit 120, the stray magnetic field is generated from the magnetic beads 10. By this stray magnetic field being applied on the magnetoresistive effect element 4, the magnetization direction of the free layer 64 changes and as a result the resistance value of the magnetoresistive effect element 4 changes and a signal is output from the biosensor 1.

The embodiment described above was described to facilitate understanding of the present invention and is intended to be illustrative and not limiting. Accordingly, each component disclosed in the above-described embodiment shall be construed to include all design modifications and equivalents that fall within the technical scope of the present invention.

Figure 12A:
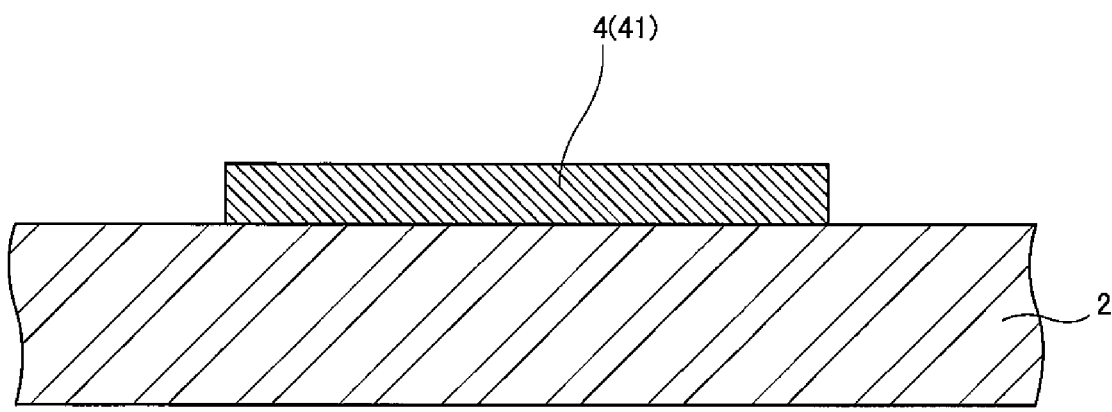
FIG. 12A is a cross-sectional view showing one step of the manufacturing process for the first aspect of the biosensor according to the embodiment of the present invention.
Figure 12B:
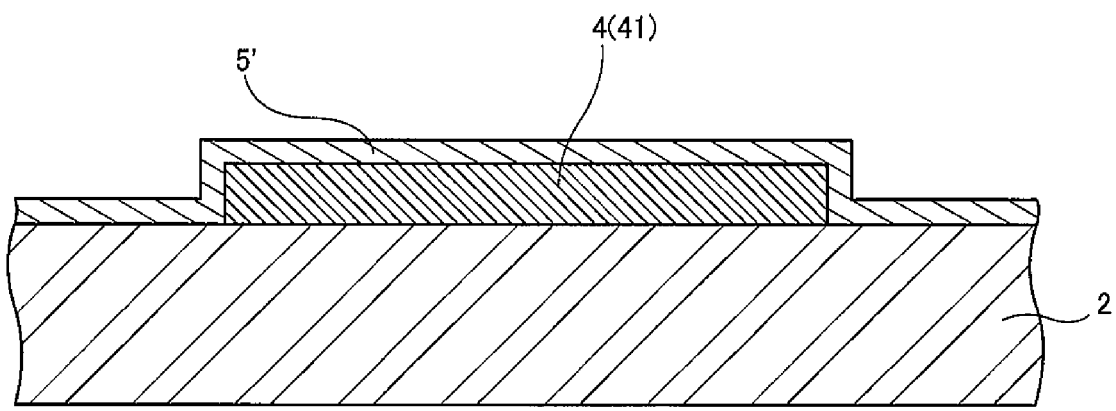
FIG. 12B is a cross-sectional view showing the step following the step shown in FIG. 12A.
Figure 12C:
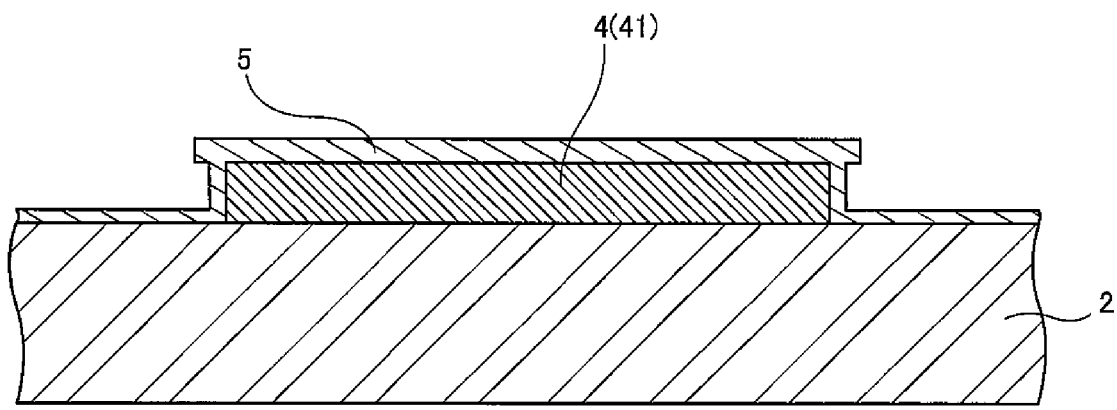
FIG. 12C is a cross-sectional view showing the step following the step shown in FIG. 12B.

In the above-described embodiment, after the linear sections 41 are formed so that the entirety of the side surfaces 4B of the linear sections 41 is substantially orthogonal to the first surface 21 of the substrate 2, and a temporary protective layer 5' that covers the linear sections 41 has been formed, by removing through milling the temporary protective layer 5' positioned between linear sections 41 adjacent when viewed along the Y direction (second direction) on the first surface 21 of the substrate 2, the second width $W_{32}$ may be made larger than the first width $W_{31}$ (see FIG. 12A FIG. 12C). In addition, by forming the protective layer with a multi-layer structure covering the linear sections 41, the second width $W_{32}$ may be made larger than the first width $W_{31}$.

In the above-described embodiment, the protective layer 5 covers the magnetoresistive effect element 4 and the first surface 21 of the substrate 2, but this is intended to be illustrative and not limiting. It is sufficient to cover the linear sections 41, for example, and it is not necessary to cover the portion where the magnetoresistive effect element 4 is not formed on the first surface 21 of the substrate 2 (the first surface 21 that is exposed).

Embodiment

Below, the present invention will be described in greater detail through embodiments or the like, but the present invention is in no way limited by the below-described embodiments or the like.

Test Example 1

Using a biosensor 1 having the configuration shown in FIG. 1 and FIG. 2A and in which the protrusion length $\Delta W/2$ of the protruding part 31 (the difference between the thickness $T_{521}$ and the thickness $T_{522}$) is 1 nm (Sample 1), 15 nm (Sample 2) and 30 nm (Sample 3), when a sample solvent including biomolecules as the detection target substance was introduced in the X direction (first direction), the flow velocity FV of the sample solvent in the side surface of the detection unit 3 and the capture rate CR of the magnetic beads 10 in the protective layer 5 were found through simulation. In addition, in contrast, using a biosensor (Sample 4) having the same configuration as Sample 1 except that there is no protruding part 31 (the difference between the thickness $T_{521}$ and the thickness $T_{522}$ is 0 nm), the flow velocity FV of the sample solvent in the side surface of the detection unit 3 and the capture rate CR of the magnetic beads 10 in the protective layer 5 were found through simulation, the same as in Samples 1~3.

Simulation Conditions

Simulation software: 3-dimensional fluid simulation software (product name: Flowsquare), simulation mode: nonreactive, uncompressed fluid mode.

Number of grid points in X direction (first direction) for discretization: 250

Number of grid points in Y direction (second direction) for discretization: 150

Length of simulation region in X direction (first direction): $0.5 \times 10^{-3}$ m Length of simulation region in Y direction (second direction): $1.5 \times 10^{-4}$ m Coefficient when determining physical time (dt) per time step: 10

Numerical calculation method: Low-precision calculation method; two-dimensional precision center difference+Euler's method (one-dimensional precision)

Relaxation factor when solving Poisson's equation: 1.8

Allowable error for completion of convergence calculation in Poisson's equation: $5.0 \times 10^{-4}$ Fluid: Reactive fluid with density changes Periodic boundary: none Pressure: $1.0 \times 10^5$ Pa Initial speed: 0.1 m/s Initial density: $1.0 \times 10^3$ kg/m$^3$ Boundary speed: 0.1 m/s Boundary density: $1.0 \times 10^3$ kg/m$^3$ Fluid viscosity coefficient (dynamic viscosity coefficient× density): $9.0 \times 10^{-4}$ kg/m·s Number of pixels per displayed lattice point: 2

When the flow velocity inside the protruding part 31 (the gap between the protruding part 31 and the substrate 2 in the Z direction) was calculated with respect to the protrusion length $\Delta W/2$ of the protruding part 31 and the flow velocity of Sample 4 was made a capture rate CR=1, the capture rates were calculated based on the flow velocities of Samples 1~3.

TABLE 1

|  | $T_{521}$(nm) | $T_{522}$(nm) | $T_{521}$:$T_{522}$ | $\Delta W/2$(nm) | FV(m/s) | CR |
|---|---|---|---|---|---|---|
| Sample 1 | 16 | 15 | 1:0.94 | 1 | 0.00580 | 3.00 |
| Sample 2 | 30 | 15 | 1:0.5 | 15 | 0.00302 | 5.70 |
| Sample 3 | 45 | 15 | 1:0.33 | 30 | 0.00237 | 7.26 |
| Sample 4 | 15 | 15 | 1:1 | 0 | 0.01720 | 1.00 |

As shown in Table 1, in Samples 1~3 having a protruding part 31 on the side surface of the detection unit 3, it was confirmed that it is possible to speed the fluid flow FV of the sample fluid in the side surface of the detection unit 3 in comparison with Sample 4, which has no protruding part 31, and it is possible to improve the capture rate CR of magnetic beads 10 on the protective layer 5. As a result, it was confirmed that by having the protruding part 31 on the side surface of the detection unit 3 and making the second width $W_{32}$ of the detection unit 3 larger than the first width $W_{31}$, it is possible to facilitate capture of the biomolecules 11 and magnetic beads 10 on the protective layer 5 and in particular on the second protective layer 52 constituting the side surface of the detection unit 3. It is further possible to make removal of the captured biomolecules 11 and magnetic beads 10 difficult through applying a gradient magnetic field or washing or the like, to detect the existence of and the quantity of biomolecules with high accuracy using the magnetic beads 10, and to control variation in detection results.

The invention claimed is:

1. A magnetic sensor used in detecting detection target substances in a sample, the magnetic sensor comprising:
   a substrate having a first surface and a second surface, which is opposite the first surface; and
   a detection unit provided on the first surface of the substrate, wherein
   the detection unit includes a magnetoresistive effect element, the resistance value of which changes in accordance with an input magnetic field, provided on the first surface of the substrate, and a protective layer that covers at least the magnetoresistive effect element, the magnetoresistive effect element is configured in a rectilinear bar form extending in a first direction on the first surface of the substrate, and ends of the magnetoresistive effect element are connected to lead electrodes, respectively, the detection unit has a first width and a second width, which are lengths in a second direction, orthogonal to the first direction, the first width is the length of the detection unit on the first surface of the substrate, the second width is the length of the top surface of the detection unit that is positioned above the first surface along a third direction orthogonal to the first surface of the substrate, and the second width is greater than the first width.

2. The magnetic sensor according to claim 1, wherein: when viewing a cross-section along the second direction with the substrate positioned on a lower side and the detection unit positioned on an upper side, the protective layer includes a first protective layer and a second protective layer;

the first protective layer is positioned on the top surface of the magnetoresistive effect element;

the second protective layer includes a first part, which is positioned along the side surface of the magnetoresistive effect element, and a second part, which is positioned above the first part; and the thickness of the second part is greater than the thickness of the first part.

3. The magnetic sensor according to claim 2, wherein the ratio of the thickness of the second part to the thickness of the first part is 1:0.05~1:0.95.

4. The magnetic sensor according to claim 2, wherein the ratio of the thickness of the first protective layer to the thickness of the second part is 1:0.05~1:1.

5. The magnetic sensor according to claim 1, wherein the angle of the side surface of the magnetoresistive effect element with respect to the first surface of the substrate is 90~135°.

6. The magnetic sensor according to claim 1, wherein the protective layer is a layered structure having a plurality of layers.

7. The magnetic sensor according to claim 1, wherein the magnetoresistive effect element is a GMR element.

8. The magnetic sensor according to claim 1, wherein the detection target substance is a biomolecule.

9. A magnetic detection device comprising:
the magnetic sensor according to claim 1; and
a support unit that supports the magnetic sensor.

10. The magnetic detection device according to claim 9, wherein a probe capable of bonding specifically with the detection target substance is present on the surface of the protective layer.

11. A magnetic detection system comprising:
the magnetic detection device according to claim 9;
a magnetic field generation unit; and
a holding unit capable of holding the sample,
wherein the magnetic detection device is provided such that the magnetic sensor can contact the sample held in the holding unit; and
the magnetic field generation unit is provided such that a magnetic field is applied on the magnetic sensor in contact with the sample held in the holding unit.

12. A magnetic sensor used in detecting detection target substances in a sample, the magnetic sensor comprising:
a substrate having a first surface and a second surface, which is opposite the first surface; and
a detection unit provided on the first surface of the substrate, wherein
the detection unit includes a magnetoresistive effect element, the resistance value of which changes in accordance with an input magnetic field, provided on the first surface of the substrate, and a protective layer that covers at least the magnetoresistive effect element,
the magnetoresistive effect element includes a plurality of parallel linear sections, which are spaced apart from one another and extend in a first direction on the first surface of the substrate, and ends of adjacent ones of the linear sections are connected by lead electrodes,
the detection unit has a first width and a second width, which are lengths in a second direction, orthogonal to the first direction, the first width is the length of the detection unit on the first surface of the substrate, the second width is the length of the top surface of the detection unit that is positioned above the first surface along a third direction orthogonal to the first surface of the substrate, and the second width is greater than the first width.

13. A magnetic sensor used in detecting detection target substances in a sample, the magnetic sensor comprising:
a substrate having a first surface and a second surface, which is opposite the first surface; and
a detection unit provided on the first surface of the substrate, wherein
the detection unit includes a magnetoresistive effect element, the resistance value of which changes in accordance with an input magnetic field, provided on the first surface of the substrate, and a protective layer that covers at least the magnetoresistive effect element,
the entirety of the magnetoresistive effect element is configured in a rectilinear bar form extending in a first direction on the first surface of the substrate,
the detection unit has a first width and a second width, which are lengths in a second direction, orthogonal to the first direction, the first width is the length of the detection unit on the first surface of the substrate, the second width is the length of the top surface of the detection unit that is positioned above the first surface along a third direction orthogonal to the first surface of the substrate, and the second width is greater than the first width.

* * * * *